United States Patent [19]
>
> Sisti et al.
>
> [11] 4,269,608
>
> [45] May 26, 1981

[54] METHOD AND DEVICE FOR SAMPLE INJECTION UNDER CONTROLLED CONDITIONS OF TEMPERATURE PROFILE INTO GAS CHROMATOGRAPHIC COLUMNS

[75] Inventors: Giorgio Sisti, Melzo, Italy; Sorin Trestianu, Iselles, Belgium; Mario Galli, Legnano, Italy

[73] Assignee: Carlo Erba Strumentazione S.p.A., Italy

[21] Appl. No.: 62,927

[22] Filed: Aug. 2, 1979

[30] Foreign Application Priority Data

Sep. 26, 1978 [IT] Italy .............................. 28092 A/78
Nov. 7, 1978 [IT] Italy .............................. 29498 A/78

[51] Int. Cl.³ .......................................... B01A 15/08
[52] U.S. Cl. ...................................... 55/67; 55/197; 73/422 GC
[58] Field of Search .................. 55/67, 386, 197; 210/198 C; 73/422 GC, 23.1 C

[56] References Cited

U.S. PATENT DOCUMENTS

| | | | |
|---|---|---|---|
| 3,719,084 | 3/1973 | Walker | 55/197 X |
| 3,841,059 | 10/1974 | McCabe | 55/197 |
| 4,123,236 | 10/1978 | Hirschfeld | 55/197 |

OTHER PUBLICATIONS

Sampling Techniques in Capillary Gas Chromatography by Schomburg et al., in Journal of Chromatography, 142 (1977), 87-102.
Aspects of Double Column Gas Chromatography with Glass Capillaries Involving Intermediate Trapping, by Schomburg et al., 112 (1975), 205-217.
Gas Phase Chromatography, vol. 1, by Kaiser, Butterworth Pub., Washington, D.C., p. 97, 1963.

*Primary Examiner*—John Adee
*Attorney, Agent, or Firm*—Lerner, David, Littenberg & Samuel

[57] ABSTRACT

A method and device for sample injections into a gas chromatographic column, wherein, in order to achieve sample trapping and solvent effects, the injection zone and an initial portion of the column are kept at a low temperature and then a quick temperature change is performed at the end of said initial portion. The cooling action is preferably performed by a cooling fluid acting outside the injector and column, while said temperature change is obtained by a suitable thermoregulation of the oven wherein said gas chromatographic column is housed.

24 Claims, 7 Drawing Figures

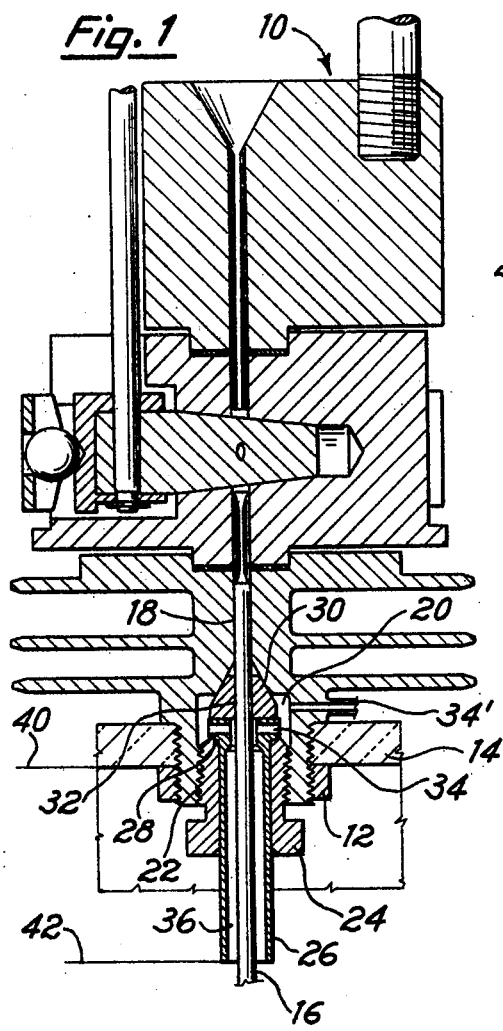
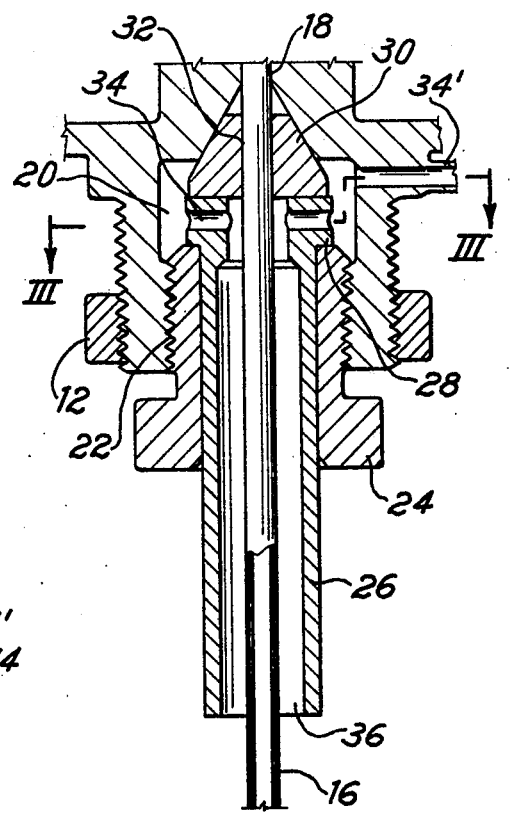
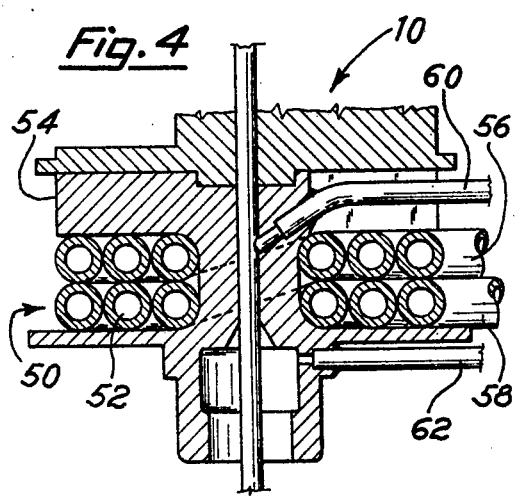
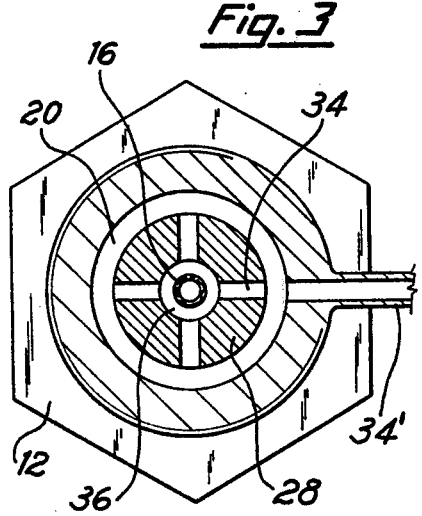

METHOD AND DEVICE FOR SAMPLE INJECTION UNDER CONTROLLED CONDITIONS OF TEMPERATURE PROFILE INTO GAS CHROMATOGRAPHIC COLUMNS

BACKGROUND OF THE INVENTION

1. Field of the Invention

This invention concerns a method and a device for performing sample injection under controlled conditions of the temperature profile into gas chromatographic columns, in order to avoid unwanted volatilizations of the sample compounds outside the injection syringe needle, in case of injection by means of "on column" type injectors, for example of the type described by Grob & Grob (Journal of Chromatography 151, page 311 (1978)), and also to ensure efficient "trapping" effect and suitable vaporization of the sample compounds entrapped in the initial part of the chromatographic column. The mentioned trapping effect may be obtained, according to the invention, not only by means of the above mentioned injectors, but also using other types of injectors or sample injection systems (for instance, split/split-less injection) used for capillary columns or packed columns. As it was proved in practice, in case of injectors of the above mentioned "on column" type, it is important that no unwanted volatilization of the sample compounds occurs during the sample injection into the column; these volatilizations may occur in case the needle temperature, and therefore the sample temperature, exceeds certain limits during the injection or at the column inlet.

2. Description of the Prior Art

As it is well known practically all injection systems for liquid samples, presently used in gas chromatography cannot carry out suitable sample injection without an additional "trapping" operation. This is due to the fact that, frequently, the sample volumes exceed the maximum values required and accepted to assure the chromatographic system efficiency.

Therefore, part of the gas chromatographic capillary column initial section is used as cold trap, causing condensation and/or solution of the sample compounds. Up to now, this is practically achieved by gradually freeing the components by means of a suitable temperature program of the oven where the column is positioned.

This trapping effect is useful when a split-less type injection is used, but it very often results advantageous even during the usual splitter-type injection. When diluted samples are injected using the split-less injection system, part of the solvent is condensed together with the sample compounds, thus increasing the trapping capacity of the column initial section part and usually determining a good definition of the peaks indicating the sample compounds during analysis. However, this solvent effect has sometimes undesired consequences. If an "on column" injection system is used, as previously indicated, the samples are directly injected as diluted solutions at the inlet part of the capillary column. In this case, too, the compounds must be entrapped in a zone of the column near the injection port and the operation must be carried out in such a way that most of the solvent is evaporated in a sufficiently slow way in order to avoid creation of a shock wave due to sudden vaporization, but anyway sufficiently rapidly to avoid formation of a liquid cap moving downwards through the column.

The presently used trapping method requires cooling of the whole column and therefore of the whole oven where the column is placed in order to obtain the above mentioned effects of trap and solvent. The method proposed according to this invention, on the contrary, enables to obtain the effects of both trap and solvent by controlling the temperature of a more or less long section of the column initial part, without altering the oven temperature conditions. Moreover, the above mentioned method versus the known technique also has the advantages of allowing to bring the column initial part to any temperature, for instance −80° C., to save power and time in comparison with conventional procedure and to perform quick temperature change in the column initial part, with limited power consumption, thanks to small thermal inertia of the whole system.

SUMMARY OF THE INVENTION

Therefore, the object of this invention is to propose a method and a device for sample injection into gas chromatographic columns, which enable to avoid the drawbacks of the existing systems and, particularly, allow on one side to achieve an effective trapping effect and on the other to prevent unwanted volatilization of the sample compounds, without any need to control the operative conditions of the oven in which the gas chromatographic column is placed.

Now, it has been surprisingly noticed that the above mentioned objects of the invention are achieved by injecting the samples into the gas chromatographic column under controlled conditions of the temperature profile at the column inlet, as performed by keeping at a desired temperature the injection port and an initial part of the column, having a preset length, and also by quickly changing the temperature immediately under this initial part, so to reach the temperature of the oven where the column is positioned. Consequently, during the most usual operations, the point in general is to keep the temperature of the injected sample low during the whole tract and the injection period and in the column initial part, so allowing a rapid temperature increase up to the oven temperature, once the sample has overcome this initial part of the column. This temperature profile control, according to the invention, allowing to achieve the objects and advantages of same, may be obtained in practice, according to a first embodiment of the invention, by keeping the injection zone and the column initial part away from the oven, for example by lifting them up above the oven for part or all the sample injection time, then restoring normal operative conditions between column and oven, to cause this rapid temperature change.

According to another and preferred embodiment of this invention, the temperature profile control may be obtained by introducing a fluid current, which laps on the column head and coaxially follows the latter for the above mentioned initial part of a preset length. This method may be adopted in practice using a particularly simple and efficient device, consisting of a jacket near the column head, surrounding the column and at a certain distance from it; this jacket extends as far as a predetermined length along the column and forms with the latter an hollow space open at one end and connected, at the opposite end, to a source supplying a fluid at controlled temperature. Generally, the jacket is open towards the low part of the column, namely towards the oven, and the fluid, for instance compressed air, is supplied at the opposite side, namely at the upper end of the jacket.

According to another embodiment, this method may be carried-out by using a device consisting of a coil axially extending on the injector lower section, this coil being fed with a liquid or gaseous fluid, kept at a suitable temperature, coming from a suitable source and discharged outside the system, possibly in close circuit with a cooling medium.

It has been surprisingly noticed that, by complying with the principles of this invention, it is possible to prevent slow evaporation of the sample compounds in the syringe needle during injection, (obviously provided that operative conditions are exactly chosen) with rapid vaporization of the sample compounds in the gaseous phase, without any shock wave arising, and this because heating time, though short, is long enough to prevent this type of unwanted processes, considering the reduced amount of sample usually injected into the column. Besides that, this invention allows to obtain a suitable vaporization speed of the solvent and the sample components injected and/or condensed (entrapped) in the column inlet part, so avoiding the drawbacks caused by too reduced or too high vaporization speed. Finally, it is possible to easily perform isothermal operations, considering that reinjection of the entrapped compounds, starting from the trap, is pratically instant if the oven temperature is kept sufficiently high. It should be noticed that in literature a trap for capillary column has already been proposed, in particular by Schomburg (G. Schomburg, H. Husmann and F. Weeke, Journal of Chromatography 112, page 205 (1975)), but anyway this known system is used only for forming a trap for the components passing from one chromatography column to another and it is not used, as in this invention, to control the temperature profile at the injection port and at least along the final section of the injector. Moreover, this known system requires an additional fragile and complicated device, which cannot be completely integrated into the injection system as in the case of the device according to this invention. The latter still has another advantage, besides a considerable stoutness and ease of handling, as it allows to control a column section of desired length by simply substituting a nut, that is by simply substituting the jacket forming the hollow space, in which the temperature controlling current flows, with another having a greater or smaller length.

BRIEF DESCRIPTION OF THE DRAWINGS

FIG. 1 is an axial section of an injector to which a temperature control device is applied.

FIG. 2 is a section, similar to that of FIG. 1 but of a larger scale, and illustrating more in detail the control device.

FIG. 3 is a section along line III—III of FIG. 2.

FIG. 4 illustrates, partially in section, the device according to the invention in a second exemplifying embodiment.

DESCRIPTION OF THE PREFERRED EMBODIMENT

Figure 5:
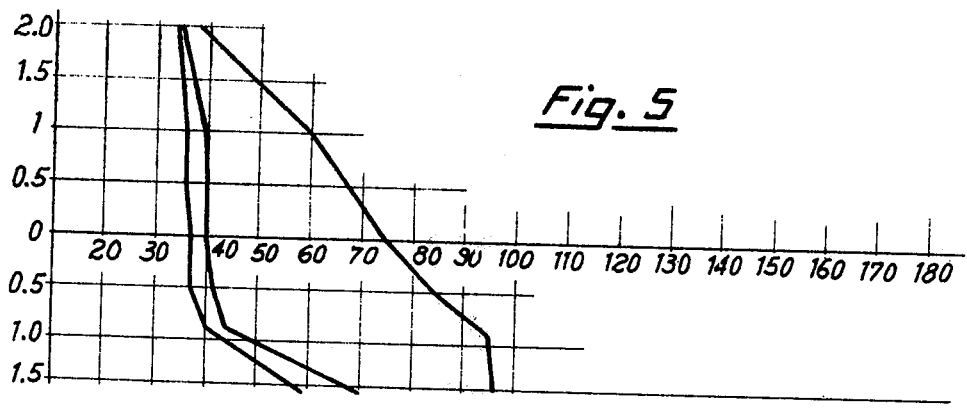
FIGS. 5 to 7 are graphs illustrating the temperature profile during injection into a gas chromatographic column under different operative conditions.

FIG. 1 illustrates, in axial section, an injector for gas chromatographic columns of the already known "on column" type, for instance of the above mentioned Grob type, generally indicated by 10. The injector, which is not herein described more in detail, is fastened with a nut 12 to the oven body 14 in which a gas chromatographic column 16 is housed. The injector 10 has an internal calibrated channel which leads to a lower opening 20, open towards the oven.

According to the invention, this opening has a threaded part 22 where an internally threaded nut 24 is fitted; the nut is in turn steadily connected to a small tube 26 ending in its upper end with a head 28 fitted with a cone-shaped piece 30 capable of airtightly mating with a countersunk zone connecting the channel 18 to the opening 20, under the sealing action of nut 24.

The cone-shaped piece 30 has a passage 32 to connect the channel 18 to the column 16 inlet, while the head 28 houses a distribution chamber, surrounding the column 16 and connected by means of at least one tube 34 to the opening 20, which is in turn connected with the outside by means of a tube or connector 34'.

This distribution chamber downwardly communicates with an airtight hollow space 36 between the column 16 internal surface and the small tube 26 internal surface, the diameters of which are consequently differentiated; this hollow space downwardly opens towards the oven 14. As shown in the drawings, the small tube 26, and therefore the hollow space 36, extend for a predetermined length coaxially to the column 16 inside the oven 14; the length of this small tube, together with the fluidodynamic and temperature characteristics of the fluid, determines the length of the section in which the sample injection temperature is controlled, and the above mentioned effects of trap and solvent occur.

In correspondence with the small tubes 34, 34', a current of fluid at a controlled temperature is injected, for example, even if not necessarily, compressed air. This current laps on the external walls of the column 16, flowing inside the hollow space 36 through the small tube 26.

In the embodiment of FIG. 4, the lower section of the injector body 10 has a housing 50 in which there is a coil 52 capable of transmitting or drawing heat from the injector through a section 54 of the latter body. The inlet and outlet ducts 56 and 58 of coil 52 are respectively connected to a suitable source of liquid or gaseous fluid and to a discharge, or possibly in close circuit with a heat exchanging device.

Reference 60 indicates the "carrier" introduction duct, while 62 indicates a duct through which air or other gas may be introduced, alternatively or jointly with the profile temperature control carried out by means of coil 52.

Figure 6:
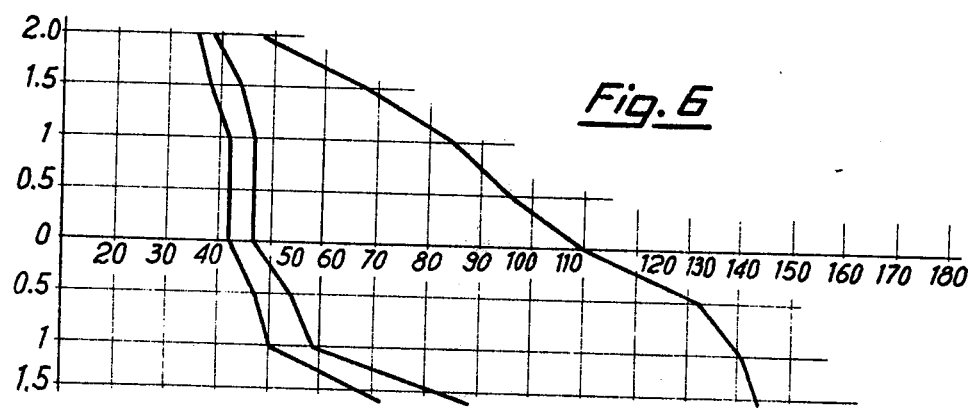
Figure 7:
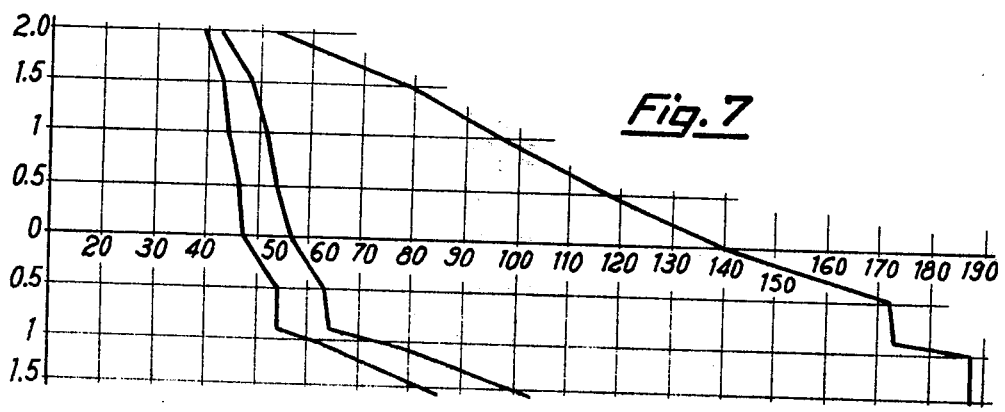

It has been surprisingly noticed that, by performing the sample injection as usual through the injector 10, the previously described advantageous effects of the invention occur, and in particular it is possible to avoid any unwanted volatilization of the sample compounds before they enter the column and an efficient trapping effect with controlled vaporization of the sample compounds is obtained. This effect occurs not only with "on column" injectors, but also with the other previously mentioned types of injectors. FIGS. 4, 5 and 6 report three graphs illustrating the temperature profile in a system like the one of FIG. 1, with and without the device according to the invention, respectively.

The graphs report on the abscissae the sample temperatures (in °C.) in different points of the system and on the ordinates the distances (in cm) from point 40 of FIG. 1, the free end of the small tube 36 being at 0.8 cm from point 40.

The curve on the left indicates the temperature profile when the device according to the invention is fed by an air current at 2.5 Kg/cm², the curve at the center indicates the same profile with the air current at 1 Kg/cm² and the curve on the right indicates, as a comparison, the profile of an injector without the device described in the invention. The graphs reported in the three figures were recorded when the oven was at temperatures of 100°, 150° and 200° C. respectively. It should be understood that the method and the device according to this invention may be used also with other systems and apparatuses for sample injection into gas chromatographic columns and that the temperature profile control may be performed by using whatever suitable fluid at whatever suitable temperature, even at temperature exceeding the column temperature. All these applicative variants together with possible constructive variants of the device, specially for making it suitable for different sample injection systems, must be considered as a part of this invention.

We claim:

1. A method for on-column injection of a liquid sample into a gas chromatographic capillary column, which column is at a gas chromatographic temperature such that vaporization of and separation of said liquid sample would normally occur, comprising
   (1) injecting said sample in the initial portion of said gas chromatographic column by means of an injection device inserted into an injector duct of an on-column injector;
   (2) cooling said sample in the injector duct and in a predetermined length of the gas chromatographic column to maintain a temperature profile of the sample so as to avoid vaporization of the sample in the injector duct, to ensure a desired rate of vaporization of the sample in said gas chromatographic column, and to trap inside said gas chromatographic column any back expulsion occurring during said injection step, said cooling being performed by at least one cooling fluid in thermal communication with said injector duct and/or said predetermined length of said gas chromatographic column; and
   (3) maintaining such cooling at least until completion of said injecting step.

2. A method according to claim 1, wherein said cooling fluid flows coaxially around the exterior of the injector duct.

3. A method according to claim 1, wherein a first cooling fluid flows through a coil about the injector duct and a second cooling fluid flows coaxially about the exterior of the injector duct and/or the predetermined length of the gas chromatographic column.

4. A method according to claim 1, wherein a first cooling fluid flows on cooling fins in thermal communication with said injector duct and a second cooling fluid flows coaxially about the exterior of said predetermined length of said gas chromatographic column.

5. A method according to claim 3 or 4, wherein said first cooling fluid flows continuously and said second cooling fluid flows temporarily at least during said injection step.

6. A method according to claim 2 or 3, wherein the cooling fluid flowing coaxially about the exterior of the injector duct and the predetermined length of the gas chromatographic column is flowing in the same general direction as the sample does when the sample vaporizes.

7. An injector system for on-column injection of a liquid sample into a gas chromatographic capillary column which is placed inside a column oven at a temperature such that vaporization of and separation of said liquid sample would normally occur inside the column, comprising
   on-column injector means having an injector duct connected to the initial portion of said gas chromatographic column for guiding an injection device into said gas chromatographic column, and,
   at least one cooling means in thermal communication with said injector duct and/or with a predetermined length of said gas chromatographic column ending in said oven, for maintaining a temperature profile so as to avoid vaporization of said liquid sample in said injector duct, to assure a desired rate of vaporization of said sample in said column, and to trap inside said column any back expulsion of said sample at least during injection of said liquid sample.

8. An injector system according to claim 7, wherein said cooling means comprises a hollow jacket disposed about said injector duct and/or said predetermined length of said gas chromatographic column, through which jacket a cooling fluid is passed.

9. An injector system according to claim 8, wherein said jacket comprises a hollow tube coaxial with said injector duct and/or said column, said tube having an internal diameter larger than the external diameter of said injector duct and/or said column and said tube being provided with connection to a cooling fluid source.

10. An injector system according to claim 9, wherein said hollow tube includes a cone-shaped member, and wherein said cooling means also comprises a countersunk zone adapted to substantially mate with said cone-shaped member to form a hermetic seal for the capillary column.

11. An injector system according to claim 10, wherein said cooling means include mating threaded members which threaded members when threaded together cooperate with said cone-shaped member to press said cone-shaped member into said countersunk zone and thereby form said hermetic seal.

12. An injector system according to claim 8, wherein said cooling fluid is ambient air under pressure.

13. An injector system according to claim 7, wherein said cooling means comprises a coil about and in thermal communication with said injector duct and said predetermined length of said gas chromatographic column, said coil being connected to a source of cooling fluid and to an exhaust for passage of said cooling fluid through said coil.

14. An injector system according to claim 13, wherein said exhaust is connected in a closed circuit to said source by means of a cooling fluid device.

15. An injector system according to claim 14, wherein said fluid cooling device is a heat exchanging device.

16. A method for on-column injection of a liquid sample into a gas chromatographic capillary column which column is at a gas chromatographic temperature such that vaporization of and separation of said liquid sample would normally occur, comprising
   (1) injecting said sample into the initial portion of said gas chromatographic column by means of an injection device inserted into an injector duct of an on-column injector;
   (2) cooling said sample in the injector duct and the predetermined length of the gas chromatographic column to maintain the temperature profile of the sample so as to avoid vaporization of the sample in the on-column injector during said injecting step by a first cooling fluid flowing through a coil about the injector duct and a second cooling fluid flowing coaxially about the exterior of the injector duct and the predetermined length of the gas chromatographic column; and (3) maintaining such cooling at least until completion of said injecting step.

17. A method for on-column injection of a liquid sample into a gas chromatographic capillary column, at least a portion of which is disposed inside a column oven at a temperature such that vaporization of and separation of said liquid sample would normally occur inside the column, comprising the steps of injecting said sample into the initial part of the gas chromatographic column by means of an injection device; and cooling said sample in a predetermined length of said gas chromatographic column including said initial part at least until said injecting step is completed to maintain a temperature profile of said predetermined length sufficient to ensure a desired rate of vaporization of the sample in said column, and sufficient to trap in said predetermined part downstream of said initial part any back expulsion of said sample.

18. An injector system according to claim 8, wherein said cooling means comprises a coil about and in thermal communication with at least a portion of said injector duct, said coil being connected to a source of a first cooling fluid and to an exhaust for passage of said cooling fluid through said coil, and a hollow jacket at least about said predetermined length of said gas chromatographic column, through which jacket a second cooling fluid passes and flows along the column inside the oven.

19. An injector system according to claim 8, wherein said cooling means comprises cooling fins in thermal communication with said injector duct and said predetermined length of said gas chromatographic column, said fins being fed by a cooling fluid.

20. An injector system according to claim 8, wherein said cooling means comprises cooling fins in thermal communication with at least a portion of said injector duct, said fins being fed by a first cooling fluid, and a hollow jacket at least about said predetermined length of said chromatographic column, through which jacket a second cooling fluid passes and flows along the column inside the oven.

21. An injector system for on-column injection of a liquid sample into a gas chromatographic capillary column which is placed in a column oven at a termperature such that vaporization of and separation of said liquid sample would normally occur, comprising (1) on-column injector means having an injector duct connected to the initial portion of said gas chromatographic column for guiding an injection device into said initial portion;

(2) a hollow jacket about said injector duct and a predetermined length of said gas chromatographic column, through which jacket a cooling fluid is passed; and (3) a coil about and in thermal communication with said injector duct, said coil being connected to a source of cooling fluid and to an exhaust for passage of said cooling fluid through said coil.

22. An injector system for on-column injection of a liquid sample into a gas chromatographic column at least a portion of which is disposed in a column oven having means to heat said column to a temperature such that vaporization of and separation of said liquid sample would normally occur inside said column, comprising at least one cooling means in thermal communication with a predetermined length of said gas chromatographic column including the initial part of said gas chromatographic column where said sample is to be injected for cooling said sample in said predetermined length to maintain a temperature profile of said sample along said predetermined length sufficient to ensure a desired rate of vaporization in said column and sufficient to trap in said predetermined length downstream of said initial part any back expulsion of said sample.

23. An injector system according to claim 7 or 8, wherein said injector means includes an injector needle.

24. A method according to claim 1, wherein said cooling fluid flows through a coil about the injector duct and the predetermined length of the gas chromatographic column.

* * * * *